US008034325B2

(12) United States Patent
Crutchley et al.

(10) Patent No.: US 8,034,325 B2
(45) Date of Patent: Oct. 11, 2011

(54) POWDER FORMED OF PARTICLES OF BILIQUID FOAM ENTRAPPED WITHIN POLYMERIC MATRIX

(75) Inventors: Nigel Stuart Crutchley, Loughton (GB); David Charles Fletcher Gladman, Farnham (GB); Stephen John Lenon, Guildford (GB)

(73) Assignee: Drug Delivery Solutions Limited, Letterhead, Surrey (GB)

( * ) Notice: Subject to any disclaimer, the term of this patent is extended or adjusted under 35 U.S.C. 154(b) by 966 days.

(21) Appl. No.: 10/517,208

(22) PCT Filed: Jun. 24, 2003

(86) PCT No.: PCT/GB03/02713
§ 371 (c)(1),
(2), (4) Date: Dec. 8, 2004

(87) PCT Pub. No.: WO2004/002436
PCT Pub. Date: Jan. 8, 2004

(65) Prior Publication Data
US 2005/0238676 A1    Oct. 27, 2005

(30) Foreign Application Priority Data
Jun. 26, 2002    (GB) .................................. 0214793.2

(51) Int. Cl.
*A61L 9/00*    (2006.01)
*A61K 8/02*    (2006.01)
*B01F 3/04*    (2006.01)
*B05D 5/00*    (2006.01)
*B05D 3/02*    (2006.01)
*A61F 13/15*    (2006.01)

(52) U.S. Cl. ...................... 424/76.1; 424/76.2; 424/76.3; 424/401; 427/243; 427/244; 427/372.2; 516/10; 604/374

(58) Field of Classification Search .................... 424/76; 427/243; 503/200; 525/71
See application file for complete search history.

(56) References Cited

U.S. PATENT DOCUMENTS

| | | | | |
|---|---|---|---|---|
| 3,016,308 A | * | 1/1962 | Macaulay | 503/200 |
| 3,549,555 A | * | 12/1970 | Jensen et al. | 428/402.21 |
| 4,486,333 A | * | 12/1984 | Sebba | 516/14 |
| 4,986,429 A | | 1/1991 | Singleton, Jr. | |
| 4,999,198 A | * | 3/1991 | Barnett et al. | 424/449 |
| 6,165,479 A | * | 12/2000 | Wheeler | 424/400 |
| 6,312,760 B1 | * | 11/2001 | Wheeler | 427/243 |
| 6,358,493 B1 | | 3/2002 | Birkel et al. | |
| 6,416,751 B1 | | 7/2002 | Roulier et al. | |

FOREIGN PATENT DOCUMENTS
DE    10107217    11/2001
* cited by examiner

*Primary Examiner* — Robert A Wax
*Assistant Examiner* — Jeffrey T Palenik
(74) *Attorney, Agent, or Firm* — Rissman Hendricks & Oliverio LLP

(57) ABSTRACT

A discrete powder which includes particles in which a biliquid foam has been entrapped within a matrix of a polymeric material. A process for the preparation of these discrete powders includes the steps of: i) preparing a biliquid foam, ii) forming a dispersion of the biliquid foam in an aqueous solution, suspension or dispersion of a polymeric material, and iii) subjecting the dispersion to drying under conditions such that a discrete powder is formed.

16 Claims, No Drawings

POWDER FORMED OF PARTICLES OF BILIQUID FOAM ENTRAPPED WITHIN POLYMERIC MATRIX

BACKGROUND OF THE INVENTION

1. Field of the Invention

The present invention relates to biliquid foam entrapment and, in particular, to a biliquid foam entrapped within a matrix of a polymeric material which is in the form of a discrete powder.

2. The Prior Art

The entrapment of oils or oil soluble substances (especially perfumes and coloured dye precursors) in microcapsules and their subsequent coating onto paper and other surfaces is well known in the art. Microcapsules of this type comprise individual droplets of oil or oil soluble substances (of size ranging from sub-micrometer to tens of millimeters in diameter) around which polymer walls have been formed by one of a number of chemical processes. Usually such microcapsules are prepared as an aqueous suspension which is then capable, with the addition of suitable modifying reagents, of being sprayed or printed onto paper and other surfaces. The object in so doing is usually to prevent the evaporation of volatile substances (for example, perfumes) or the degradation or chemical reaction of oil soluble species (for example, colourless dye precursors) until the microcapsules are broken by the application of shear forces by scratching or scraping the coated surface with the consequent release of their contents. Such coatings find major uses, for example, in the forms of "scratch and sniff" perfume coatings or NCR (No Carbon Required) paper.

However, these microcapsules suffer from a number of disadvantages.

Firstly, the process by which microcapsules are formed is a lengthy and uncertain one in which control over temperature, pH and the absence of any form of contamination is essential. The formation of microcapsules, for example, by complex coacervation from gelatin and an anionic complexing species such as gum acacia takes many hours and demands very close control of pH, temperature and cooling rate. Similarly, the formation of microcapsule walls from aminoplast resins, such as melamine-formaldehyde or urea-formaldehyde takes at least eight hours during which precise control over all controllable parameters needs to be effected. Moreover, the effectiveness and completeness of any individual encapsulation process (and therefore the quality of the microcapsules so formed) depends largely on the chemical nature of the oil and/or oil soluble substances being encapsulated.

A further disadvantage of microcapsulation is that the thickness and therefore the strength of the microcapsule wall is variable and is not easily is controllable and varies with the nature of the oil or oil-soluble substances being encapsulated. Thus microcapsules made by the same process but from different oils may have widely differing strengths and resistance to breakage during the printing process and during subsequent storage and use.

A yet further disadvantage of microencapsulation is the limited number of chemical processes and the limited number and type of polymeric wall materials which are available to form them. The choice as to the properties of the wall materials is consequently limited with regard to their flexibility, tensile strength, permeability, chemical inertness, mammalian toxicity and other properties including solubility and melting point (if any). In addition, some of the chemicals commonly used in the wall forming process are themselves highly irritating and may themselves be toxic such, for example, as the use or release of formaldehyde (a potential carcinogen) during the manufacture of aminoplast resin walls. Moreover, the remaining traces of formalin in the resulting microcapsule suspension are virtually impossible to eliminate to below acceptable levels for uses of microcapsules and requires special precautions to be taken during the manufacturing process.

Whilst many of the processes to produce microcapsules produce dispersions of the microcapsules in a fluid medium, they can also be produced in the form of a powder.

Other methods of encapsulating oil within a powder are generally based upon the drying of an oil-in-water dispersion. Examples of this prior art include EP-B-0938932 which discloses a process for manufacturing a cosmetic and/or dermatological powder in which an oil-in-water dispersion comprising at least one modified starch is dehydrated to form a powder and U.S. Pat. No. 6,129,906 in which a granular powder is formed by spray drying an aqueous dispersion of a silicone oil and a water-soluble carrier, the silicone oil being present in the dispersion as discrete droplets having a droplet size in the range of from 0.5 µm to 20 µm.

WO 99/05299 discloses a surface coating in which droplets of a non-polar substance are trapped within a polymer film, the surface coating being prepared by drying a dispersion of a film forming polymer containing droplets of a suspended biliquid foam or emulsion. Surface coatings only are disclosed and this reference does not teach the drying of the dispersions to form a powder.

SUMMARY OF THE INVENTION

We have now developed a discrete powder which is based upon the encapsulation of a biliquid foam.

Accordingly, in one aspect of the present invention provides a discrete powder which comprises particles in which a biliquid foam has been entrapped within a matrix of a polymeric material.

In another aspect the present invention provides a process for the preparation of a discrete powder which comprises a biliquid foam entrapped within a matrix of a polymeric material, which process comprises the steps of:
  i) preparing a biliquid foam,
  ii) forming a dispersion of the biliquid foam in an aqueous solution, suspension or dispersion of a polymeric material, and
  iii) subjecting the dispersion to drying under conditions such that a discrete powder is formed.

The discrete powder of the present invention is preferably produced by spray drying of the dispersion.

Biliquid foams are known in the art and are described in the following literature references by Sebba: "Biliquid foams", J. Colloid and Interface Science, 40 (1972) 468-474; and "The Behaviour of Minute Oil Droplets Encapsulated in a Water Film", Colloid Polymer Sciences, 257 (1979) 392-396. Neither of these articles suggest that biliquid foams might be used in the preparation of spray dried powders.

U.S. Pat. No. 4,486,333 to Sebba describes a particular method for the preparation of biliquid foams by agitating a hydrogen bonded liquid containing a soluble surfactant to produce a gas foam and intermittently adding to the gas foam a non-polar liquid which is immiscible with the hydrogen bonded liquid, the surfactant-containing hydrogen bonded liquid being selected to provide a spreading coefficient equal to or greater than zero.

The oil-based biliquid foam used in the spray dried powders of the present invention well preferably comprise from 70 to 95% by weight of the oil phase and from 5 to 30% by weight of the continuous phase. A surfactant to stabilise the biliquid foam may also be included in an amount of from 0.01 to 3%, preferably from 0.1 to 1% based on the total weight of the biliquid foam. The surfactant may dissolve in either the oil phase, the continuous phase or both phases of the biliquid foam. Generally, the level of surfactant used in the formation of the biliquid foams is lower than the level used in the preparation of conventional dry emulsion systems.

Oils which may be used in the biliquid foam will in general be substantially water immiscible and liquid at room temperature and may be, for example, a cyclomethicone, dimethicone, phenyl trimethicone, dimethiconol, dimethicone copolyol, trimethylsiloxy-silicate, an emollient ester such as isopropyl isostearate, lanolate, myristate or palmitate, or octyl palmitate, a glyceride such as avocado oil, coconut oil, soybean oil or sunflower oil, or a caprylic/capric triglyceride, a lanolin oil, orange oil, mineral oil or natural oil, or oleyl alcohol, or any other oil generally known for this purpose, or mixtures of the foregoing. It will be understood that the present invention enables oils to be incorporated into the powder which would normally be difficult to incorporate into conventional dry emulsion systems.

It will be understood that the oil phase of the biliquid foam may contain or consist of one or more active ingredients such as fragrances, flavours, deodorisers, perfumes, pharmaceuticals, sunscreens, dyes, pesticides, insect repellants, herbicides, etc.

The biliquid foam may contain, as described above, a low level of a surfactant which may be, for example:— a cationic surfactant such as an amidoamine, a quaternary ammonium compound or a sulphonium salt;

an amphoteric surfactant such as an acylamino-acid, an N-substituted alkylamine, an N-alkyl-$\beta$-amino-propionate, an N-alkylbetaine, an alkylimidazoline or a sulphobetaine;

an anionic surfactant such as an acyl-lactate, N-acylsarcosinate, alkyl-carboxylate (either mono- or polyvalent), alkyl ether carboxylate, N-alkyl-glutamate, fatty acid-peptide condensate, phosphated ethoxylated alcohol, alkyl sulphate, ethoxylated alkyl sulphate, alpha-olefin sulphonate or ester-linked sulphonate;

a nonionic surfactant such as an alkanolamide, amine oxide, ester of a polyhydric (for example an ester of an ethylene, diethylene or propylene glycol, or glycerol or a polyglycerol, or sorbitan, glucose or sucrose), a polyoxyethylene or polyoxypropylene derivative of an alcohol, amide or ester, or a polyoxyethylene/polyoxypropylene block copolymer;

or a suitable compatible mixture of these surfactants.

The continuous phase of the biliquid foam is generally an aqueous phase which may include therein a is substantial level of a $C_1$-$C_4$ (water miscible) alcohol, or ethylene glycol or mixtures thereof.

The continuous phase of the biliquid foam may include therein preservatives, stabilizers or other materials known in the art.

Methods of producing biliquid foams are described in U.S. Pat. No. 4,486,333 involving the preliminary formation of a gas foam in order to provide a sufficiently large surface area on which the biliquid foam can subsequently be formed. It has been found that the prior formation of a gas foam is not required to manufacture a stable biliquid foam, provided that a suitable stirring mechanism is provided in the manufacturing vessel. An aspect of the present invention is the ability to manufacture biliquid foams without the preliminary formation of gas foam, by the use of a tank incorporating a suitable stirring mechanism.

Such an apparatus comprises a tank provided with a stirrer in which the stirrer blade breaks the interface between the liquid and air. A delivery device is provided through which the oil phase (water immiscible liquid), which will comprise the internal phase of the dispersion, is delivered to the tank. The design of the delivery device is such that the rate of addition of the internal phase fluid can be controlled and varied during the production process. A feature of the production process is that the internal (oil) phase is added to the stirred aqueous phase slowly at first until sufficient droplets have been formed to constitute a large, additional surface area for the more rapid formation of new droplets. At this point, the rate of addition of the oil phase may be increased.

The production process consists of the following steps:
1. The addition of one or more chosen surfactants to one or other or both phases (as previously determined by experiment)
2. The charging of the aqueous phase into the bottom of a process vessel.
3. The incorporation of the stirrer into the vessel so that it stirs the surface of the aqueous phase.
4. Adjustment of the stirrer speed to a previously determined level.
5. The slow addition of the internal phase whilst continuing to stir at the prescribed speed.
6. The speeding up of the rate of addition of the oil phase once a prescribed amount (usually between 5% and 10% of the total amount to be added) has been added.

The stirring rate and the rate of addition of the oil phase are variables, the values of which depend upon the detailed design of the manufacturing plant (in particular, the ratio of tank diameter to impeller diameter), the physico-chemical properties of the oil phase and the nature and concentrations of the chosen surfactants. These can all be pre-determined by laboratory or pilot plant experiment.

It will be understood by those skilled in the art that other manufacturing methods may be used to produce the biliquid foams, as appropriate.

In the present invention the biliquid foam is entrapped within a polymeric material and thereby forms a discrete powder. Water-dispersible or water-soluble film forming polymers of many types are well known and include cellulose derivatives (for example, carboxymethylcellulose, hydroxyethylcellulose, cetylhydroxycellulose, hydroxypropylcellulose, hydroxypropylmethylcellulose, hydroxyethylmethylcellulose and methylcellulose), gelatin, gum arabic, gum acacia, gellan gum, shellac, carragenan, natural starches, modified starches, xanthan gums, alginates, dextrins, polyvinyl alcohol, polyvinyl acetate, polyvinyl pyrollidone or polyamides and other water dispersible or water soluble film forming agents known in the art. The present invention may include the use of all the above singly or in combination. Certain of the polymers may only be water-dispersible or water-soluble at elevated temperatures and therefore in the preparation of the dispersions of the biliquid foams and during spray drying, the dispersion mixture would be used at these elevated temperatures. Industrial, food or pharmaceutical grade polymers may be used, depending upon the end use of the dried powder.

In carrying out the process of the present invention for forming a discrete powder the suspension of the biliquid foam in an aqueous solution, suspension or dispersion of the polymeric film former is dried under conditions such that a discrete powder is formed. Preferably the said dispersion is spray dried. The choice of suitable spray drying conditions will be within the knowledge of a person skilled in the art and will depend upon various factors, including the melt temperature of the polymeric material, the amount of water contained in the dispersion, the ratio of polymeric material to the biliquid foam etc. Generally the inlet temperature for the spray dryer will be in the range of from 170° to 210° C. and the outlet temperature will be in the range of from 85 to 110° C.

The dispersion which is subjected to drying may also incorporate a structuring or gelling agent therein. Any such agent must, however, shear thin when the dispersion is subjected to atomisation forces, for example during spray drying. Such a structuring or gelling agent may assist in maintaining the integrity of the dispersion prior to the drying process.

Typically, in carrying out the present invention the biliquid foam will have a mean droplet size in the range of from 1 to 45 micrometers. A biliquid foam having such a droplet size can generally be produced under low shear conditions. For the purpose of the present invention the droplet size of the majority of the droplets of the biliquid foam should preferably be further reduced to below 12 micrometers, for example by using higher shear conditions.

The biliquid foam is then mixed with an aqueous solution, suspension or dispersion of the polymeric material under conditions which generate a homogeneous dispersion. For example, using gentle stirring or using a high shear device, such as a Roto Stator mixer.

It will be understood that although spray drying is the preferred method of producing the discrete powders of the present invention, other drying techniques, such as freeze drying and fluidized bed granulation can also be used.

The discrete powders of the present invention generally incorporate high levels of oil entrapped within the polymeric material, typically from 5 to 50% by weight, preferably from 20 to 40% by weight based on the weight of the powder.

The discrete powders of the present invention will generally have a mean particle size in the range of from 5 to 150 μm. It will be understood, however, that larger particle sizes may be obtained by the use of techniques known in the art, such as granulation. The size range may then be of the order of 5 μm to 1 mm.

The invention provides a means of controlling the rate of release of the oil entrapped within the polymeric material by exercising control over the concentration and ratio to the biliquid foam of the film forming polymer in solution or suspension and thereby controlling the thickness and strength of the film forming the outside of the particles.

The invention also allows for release of the oil by dissolution of the film by contact with water or other polar solvent. For example, the powder may contain a fragrance or aromatherapy oil and be sprinkled onto water in a bath. In addition, the water-soluble or water dispersible film forming polymer may be partially or wholly crosslinked to render it partially or totally water insoluble by which means the rate of release of the entrapped biliquid foam may be controlled by the speed or absence of dissolution when the powder makes contact with water or other polar liquid in which it might otherwise be soluble. Different powders could then be mixed together in order to give a range of release rates, if required.

Alternatively, the choice of film-forming polymer may be such that it is sensitive to acidity or alkalinity so that the release of the entrapped oil may be determined by a change of pH or by the presence of another chemical species with which the film-forming polymers may react, so rendering it permeable or unstable. Alternatively, the choice of film-forming polymer may be such that it is sensitive to temperature or biological conditions. The powder may alternatively comprise a polymer which melts at a known and predetermined temperature to release the entrapped oil.

In one embodiment, the entrapped biliquid foam may comprise a perfume which, when dried into a discrete powder will behave and perform precisely as a conventional, microencapsulated "scratch and sniff" perfume as previously described. Furthermore, an encapsulating polymer may be chosen that allows the release of the perfume by diffusion over time, such as in a room fragrancing device.

In another embodiment, a perfume or deodorising composition is entrapped according to this invention in a discrete powder which is incorporated into a diaper, incontinence pad or feminine hygiene product during manufacture so that the perfume or deodorising composition is released on contact with aqueous bodily fluids when the diaper, incontinence pad or feminine hygiene product is used, thereby masking or neutralising any disagreeable odour.

In another embodiment, the powder may be provided as a dry skin wash composition containing a cleansing, moisturising or emollient oil. In this instance, the dry powder would be applied to the skin and rubbed either with or without the addition of water in order to release the entrapped from the polymer matrix.

In another embodiment, the biliquid foam comprising a household cleaning oil, such as orange oil may be entrapped in water soluble polymer powder particles on a suitable applicator together with other reagents (for example, an abrasive material, such as a pumice or water soluble antimicrobial agents) to form a dry surface which, when wetted, becomes an effective hard surface cleaning product.

In another embodiment the powder may be provided as a carpet or fabric cleaning or deodorizing composition and the oil will then comprise a suitable cleaning or deodorizing oil.

In yet another embodiment, the matrix forming polymer may comprise a brittle film which ruptures easily when deformed so releasing the entrapped non-polar substance. In one application of this embodiment, the powder may be coated onto a flexible film which may, for example, be shrunk onto the cap of a consumer product such that if the flexible film is removed, the particles rupture so releasing the non-polar substance which, in this instance, may be the colourless precursor of a coloured dye which, on release, undergoes a chemical change to become highly coloured. This embodiment thereby gives a clear indication as to whether or not a closure has been tampered with. Alternatively, the powder may be incorporated into the film forming polymer precursor during the preparation of the flexible films. The film forming polymer precursor will be chosen from suitable materials which do not dissolve the powder.

In a still further embodiment of the present invention the discrete powder particles may be granulated or formed into tablets according to techniques known in the art. In these processes the powder may be combined with one or more binders, excipients, fillers, disintegrants or other suitable materials.

The powders of the present invention may also be incorporated during extrusion of a polymer melt. In this instance the polymer system will be selected such that the polymer melt does not dissolve the polymer used in the preparation of the powders of the invention. The melt temperature of the polymer used in forming the powders will also need to be greater than that of the extruding polymer.

The oil which is incorporated into the powder may be chosen such that it boils at a given temperature, thereby rupturing the powder, or film or extruded polymer containing the powder, thereby causing a trigger release of the oil. This embodiment may be used, for example, for the release of a latent catalyst which may enable controlled chemical modification of the extruding polymer to take place.

A still further release mechanism may be the use of polymeric systems in the formation of the powders of the invention which are biodegradable, thermally degradable or photodegradable. The oil contained in the powders would then be released on degradation of the polymers.

The present invention will be further described with reference to the following Examples.

Preparation of Biliquid Foams

Preparation 1

A biliquid foam was prepared from the following ingredients.

| Ingredients | Weight (g) | % |
| --- | --- | --- |
| Aqueous Phase | | |
| Water | 396 | 9.9 |
| Sodium lauryl ether sulphate | 4 | 0.1 |
| Oil Phase | | |
| Volpo L3 | 36.4 | 0.9 |
| Medium viscosity white mineral oil | 3563.6 | 89.1 |
| Total | 4000 | 100 |

The biliquid foam was prepared by adding the oil phase to the aqueous phase and stirring with a flat bladed stirrer at 300 rpm until the mean droplet size was 15-20 micrometers.

A 1 kg sample was removed and this was stirred with a flat bladed stirrer at 500 rpm until the mean droplet size was 11 micrometers.

Preparation 2

| Ingredients | Weight (g) | % |
| --- | --- | --- |
| Aqueous Phase | | |
| Water | 148.5 | 9.9 |
| Tween 20 | 1.5 | 0.1 |
| Oil Phase | | |
| PEG25 castor oil | 13.5 | 0.9 |
| KMC | 1269.7 | 84.65 |
| Pergascript Red I-6B | 66.8 | 4.45 |
| Total | 1500.0 | 100 |

The biliquid foam was prepared by adding the oil phase to the aqueous phase and stirring with a flat bladed stirrer at 116 rpm. The mean droplet diameter was 35 micrometers. The stirrer speed was then increased to 250 rpm and stirred until the mean droplet size was less than 12 micrometers.

Preparation 3

| Ingredients | Weight (g) | % |
| --- | --- | --- |
| Aqueous Phase | | |
| Water | 47.67 | 9 |
| Sodium lauryl ether sulphate | 0.53 | 0.1 |
| Oil Phase | | |
| Laureth 3 | 4.77 | 0.9 |
| Dow Corning 200 50cst | 476.74 | 90.0 |
| Total | 529.71 | 100 |

The biliquid foam was prepared by adding the oil phase to the aqueous phase whilst stirring with a flat bladed stirrer at 200 rpm for 45 minutes.

Preparation 4

| Ingredients | Weight (g) | % |
| --- | --- | --- |
| Aqueous Phase | | |
| Water | 44.97 | 9 |
| Sodium lauryl ether sulphate | 0.5 | 0.1 |
| Kathon 1CG II | 0.03 | 0.006 |
| Oil Phase | | |
| Oleth 10 | 4.5 | 0.9 |
| Orange oil | 450.0 | 90.0 |
| Total | 500 | 100 |

The biliquid foam was prepared by adding the oil phase to the aqueous phase whilst stirring with a flat bladed stirrer at 200 rpm for 45 minutes.

Preparation 5

| Ingredients | Weight (g) | % |
| --- | --- | --- |
| Aqueous Phase | | |
| Water | 52.60 | 9.8 |
| Sodium lauryl ether sulphate | 0.532 | 0.1 |
| Kathon 1CG II | 0.026 | 0.0048 |
| Oil Phase | | |
| Etocas 25 (PEG25 Castor oil) | 4.78 | 0.9 |
| Rose oil fragrance L301844 | 478.44 | 89.2 |
| Total | 536.378 | 100 |

The biliquid foam was prepared by adding the oil phase to the aqueous phase whilst stirring with a flat bladed stirrer at 200 rpm for 45 minutes.

Preparation 6

| Ingredients | Weight (g) | % |
|---|---|---|
| Aqueous Phase | | |
| Water | 14.85 | 9.9 |
| Tween 20 | 0.15 | 0.1 |
| Oil Phase | | |
| Oleth 10 | 1.35 | 0.9 |
| Octyl methoxy cinnamate | 133.65 | 89.1 |
| Total | 150 | 100 |

The biliquid foam was prepared by adding the oil phase to the aqueous phase whilst stirring with a flat bladed stirrer at 200 rpm for 45 minutes.

Preparation 7

| Ingredients | Weight (g) | % |
|---|---|---|
| Aqueous Phase | | |
| Water | 11.29 | 8.79 |
| Tween 20 | 0.26 | 0.20 |
| Oil Phase | | |
| PEG25 castor oil | 0.64 | 0.5 |
| Oleth 10 | 0.64 | 0.5 |
| Household Fragrance oil | 115.55 | 90 |
| Total | 128.38 | 100 |

The biliquid foam was prepared by adding the oil phase to the aqueous phase whilst stirring with a flat bladed stirrer at 200 rpm for 45 minutes.

Preparation 8

| Ingredients | Weight (g) | % |
|---|---|---|
| Aqueous Phase | | |
| Water | 9 | 9 |
| Laureth 23 | 1 | 1 |
| Oil Phase | | |
| Gransil GCM-5 | 49.24 | 49.24 |
| Cetearyl isonanoate | 7.78 | 7.78 |
| Isopar K | 7.78 | 7.78 |
| Dow Corning 200 50cst | 0.97 | 0.97 |
| Gransil DMCM-5 | 24.25 | 24.25 |
| Total | 100 | 100 |

The biliquid foam was prepared by adding the oil phase to the aqueous phase and stirring with a flat bladed stirrer at 174 rpm. The stirrer speed was increased to 300 rpm to help with the inclusion of the oil before continuing to stir at 174 rpm until the mean droplet size was 11 µm.

Preparation 9

| Ingredients | Weight (g) | % |
|---|---|---|
| Aqueous Phase | | |
| Water | 9.9 | 9.9 |
| Tween 20 | 0.1 | 0.1 |
| Oil Phase | | |
| Ibuprofen | 4.5 | 4.5 |
| Isopropyl myristate | 84.5 | 84.5 |
| Laureth 3 | 1 | 1 |
| Total | 100 | 100 |

The biliquid foam was prepared by adding the oil phase (ibuprofen fully dissolved in the isopropyl myristate) to the aqueous phase and stirring with a flat bladed stirrer at 174 rpm. The preparation was stirred after the inclusion of the oil until the mean droplet size was 18 micrometers.

Preparation 10

| Ingredients | Weight (g) | % |
|---|---|---|
| Aqueous phase | | |
| Water | 49.5 | 9.9 |
| Tween 20 | 0.5 | 0.1 |
| Oil Phase | | |
| PEG25 castor oil | 2.5 | 0.5 |
| Oleth 10 | 2.5 | 0.5 |
| Household Fragrance oil | 445 | 89 |
| Total | 500 | 100 |

The biliquid foam was prepared by adding the oil phase to the aqueous phase whilst stirring with a flat bladed stirrer at 220 rpm for 60 minutes. The procedure was repeated twice more to generate three 500 g batches which were blended together for use in spray drying examples.

Preparation 11

| Ingredients | Weight (g) | % |
|---|---|---|
| Aqueous Phase | | |
| Water | 99 | 9.9 |
| Sodium lauryl ether sulphate | 1 | 0.1 |
| Oil Phase | | |
| Laureth 4 | 9 | 0.9 |
| Mineral oil with red dye | 891 | 89.1 |
| Total | 1000 | 100 |

The biliquid foam was prepared by adding the oil phase to the aqueous phase whilst stirring with a flat bladed stirrer at 110 rpm for 30 minutes. The preparation was then sheared at 230 rpm until the droplet size was less than 10 microns.

Preparation 12

| Ingredients | Weight (g) | % |
|---|---|---|
| Aqueous Phase | | |
| Water | 39.6 | 9.9 |
| Tween 20 | 0.4 | 0.1 |
| Oil Phase | | |
| Emulsifier A | 4 | 1 |
| Deodorising oil | 356 | 89 |
| Total | 500 | 100 |

The biliquid foam was prepared by adding the oil phase to the aqueous phase whilst stirring with a flat bladed stirrer at 180 rpm for 60 minutes. The preparation was stirred at 230 rpm until the droplet size was less than 10 microns.

Emulsifier A Consists of:

| | | |
|---|---|---|
| Ethoxylated isotridecanol (9EO) | | 52.52% |
| Dipropylene glycol | | 25.25% |
| PEG 40 Hydrogenated castor oil | | 22.23% |

Preparation of Dispersions and Spray Drying

EXAMPLE 1

The dispersion was prepared by stirring the biliquid foam into the aqueous polymer immediately before spray drying.

| Ingredients | Weight (g) | % |
|---|---|---|
| Preparation 1 | 76.9 | 7.7 |
| Gum acacia (30% by weight in demineralized water) | 923.1 | 92.3 |
| Total | 1000 | 100 |

| Spray drying conditions | |
|---|---|
| Pilot plant | Tests were carried out in a 1 m diameter pilot spray drying tower with downward co current air flow. Atomisation was carried out with a two fluid nozzle. |
| Total non volatiles | 34.6% |
| Oil:polymer (dry basis) | 20:80 |
| Inlet/outlet temperature | 200° C./95° C. |
| Yield | 85.2% |
| Comment | |
| Product Characterisation | |
| Nature of dry particle | Fine powder |
| Oil encapsulation | Good |
| Oil release | Moderate amount of loose oil visible on release. |
| Mean droplet size before spraying | 1.99 µm |

EXAMPLE 2

The dispersion was prepared by stirring the biliquid foam into the aqueous polymer immediately before spray drying.

| Ingredients | Weight (g) | % |
|---|---|---|
| Preparation 1 | 73.85 | 8.7 |
| PVP K30 (30% by weight in demineralized water) | 465.9 | 54.8 |
| Mowiol (5% by weight in demineralized water) | 310.6 | 36.5 |
| Total | 850.4 | 100 |

| Spray drying conditions | |
|---|---|
| Pilot plant | Tests were carried out in a 1 m diameter pilot spray drying tower with downward co current air flow. Atomisation was carried out with a two fluid nozzle. |
| Total non volatiles | 26% |
| Oil:polymer (dry basis) | 30:70 |
| Inlet/outlet temperature | 210° C./110° C. |
| Yield | about 100% |
| Comment | |
| Product Characterisation | |
| Nature of dry particle | Good |
| Oil encapsulation | Good |
| Oil release | Little visible oil. |
| Mean droplet size before spraying | 6.1 µm, peak at 11 µm. |

EXAMPLE 3

The dispersion was prepared by stirring the biliquid foam and water into the aqueous polymer immediately before spray drying.

| Ingredients | Weight (g) | % |
|---|---|---|
| Preparation 1 | 100 | 11.7 |
| Water | 74.64 | 8.7 |
| Maltodextrin (40% by weight in demineralized water) | 52.5 | 6.1 |
| PVP k30 (30% by weight in demineralized water) | 630 | 73.5 |
| Total | 847.14 | 100 |

| Spray drying conditions | |
|---|---|
| Pilot plant | Tests were carried out in a 1 m diameter pilot spray drying tower with downward co current air flow. Atomisation was carried out with a two fluid nozzle. |

| | |
|---|---|
| Total non volatiles | 35% |
| Oil:polymer (dry basis) | 30:70 |
| Inlet/outlet temperature | 185° C./85° C. increased to 90° c. |
| Yield | 17.2% |
| Comment | Product slightly damp initially but spray dried well with higher outlet temperature. |
| Product Characterisation | |
| Mature of dry particle | Good |
| Oil encapsulation | Good |
| Oil release | Slight amount of loose oil visible. |
| Mean droplet size before spraying | 1.2 μm, peak at 9 μm. |

EXAMPLE 4

The dispersion was prepared by stirring the biliquid foam and make up water into the aqueous polymer immediately before spray drying.

| Ingredients | Weight (g) | % |
|---|---|---|
| Preparation 2 | 116.67 | 11.67 |
| Water | 66.67 | 6.67 |
| PVP K30 (30% by weight in demineralized water) | 816.67 | 81.67 |
| Total | 1000 | 100 |

| Spray drying conditions | |
|---|---|
| Pilot plant | Tests were carried out in a 1 m diameter pilot spray drying tower with downward co current air flow. Atomisation was carried out with a two fluid nozzle. |
| Total non volatiles | 35% |
| Oil:polymer (dry basis) | 30:70 |
| Inlet/outlet temperature | 203° C./95° C. |
| Yield | 64.21% |
| Comment | |
| Product Characterisation | |
| Nature of dry particle | Good |
| Oil encapsulation | Good |
| Oil release | Little visible free oil. |
| Mean droplet size before spraying | 0.58 μm, peaks at 0.15, 0.7 and 12 μm. |

EXAMPLE 5

The dispersion was prepared by stirring the biliquid roam and water into the aqueous polymers immediately before spray drying.

| Ingredients | Weight (g) | % |
|---|---|---|
| Preparation 3 | 89.9 | 11.7 |
| Water | 67.1 | 8.7 |
| Maltodextrin (40% by weight in demineralized water) | 47.2 | 6.1 |
| PVP k30 (30% by weight in demineralized water) | 566.6 | 73.5 |
| Total | 770.9 | 100 |

| Spray drying conditions | |
|---|---|
| Pilot plant | Tests were carried out in a 1 m diameter pilot spray drying tower with downward co current air flow. Atomisation was carried out with a two fluid nozzle. |
| Total non volatiles | 35% |
| Oil:polymer (dry basis) | 30:70 |
| Inlet/outlet temperature | 195° C./95° C. |
| Yield | 56.6% |
| Comment | Spray dried well |
| Product Characterisation | |
| Nature of dry particle | Good |
| Oil encapsulation | Good |
| Oil release | No visible oil on surface |
| Mean droplet size before spraying | 9.9 μm |

EXAMPLE 6

The dispersion was prepared by stirring the biliquid foam and water into the aqueous polymers immediately before spray drying.

| Ingredients | Weight (g) | % |
|---|---|---|
| Preparation 4 | 105.4 | 13.7 |
| Water | 48.8 | 6.3 |
| Maltodextrin (40% by weight in demineralized water) | 614.7 | 79.9 |
| Total | 768.9 | 100 |

| Spray drying conditions | |
|---|---|
| Pilot plant | Tests were carried out in a 1 m diameter pilot spray drying tower with downward co current air flow. Atomisation was carried out with a two fluid nozzle. |
| Total non volatiles | 45% |
| Oil:polymer (dry basis) | 27.8:72.2 |
| Inlet/outlet temperature | 195° C./95° C. |
| Yield | about 100% |
| Comment | Spray dried well |

-continued

| Product Characterisation | |
|---|---|
| Nature of dry particle | Good |
| Oil encapsulation | Good |
| Oil release | Little visible oil. |
| Mean droplet size before spraying | 1.4 μm |

EXAMPLE 7

The dispersion was prepared by stirring the biliquid foam and water into the aqueous polymers immediately before spray drying.

| Ingredients | Weight (g) | % |
|---|---|---|
| Preparation 4 | 101.7 | 11.7 |
| Water | 147.1 | 16.9 |
| Maltodextrin (40% by weight in demineralized water) | 266.9 | 30.6 |
| Gum acacia | 355.9 | 40.8 |
| Total | 871.6 | 100 |

| Spray drying conditions | |
|---|---|
| Pilot plant | Tests were carried out in a 1 m diameter pilot spray drying tower with downward co current air flow. Atomisation was carried out with a two fluid nozzle. |
| Total non volatiles | 35% |
| Oil:polymer (dry basis) | 30:70 |
| Inlet/outlet temperature | 195° C./95° C. |
| Yield | 78.3% |
| Comment | Spray dried well |
| Product Characterisation | |
| Nature of dry particle | Good |
| Oil encapsulation | Good |
| Oil release | Little visible oil at surface. |
| Mean droplet size before spraying | 1.3 μm |

EXAMPLE 8

The dispersion was prepared by stirring the biliquid foam and water into the aqueous polymers immediately before spray drying.

| Ingredients | Weight (g) | % |
|---|---|---|
| Preparation 5 | 81.4 | 11.7 |
| Water | 89.3 | 12.8 |
| Maltodextrin (40% by weight in demineralized water) | 128.3 | 18.4 |
| PVP k30 (30% by weight in demineralized water) | 399.1 | 57.2 |
| Total | 698.1 | 100 |

| Spray drying conditions | |
|---|---|
| Pilot plant | Tests were carried out in a 1 m diameter pilot spray drying cower with downward co current air flow. Atomisation was carried out with a two fluid nozzle. |
| Total non volatiles | 35% |
| Oil:polymer (dry basis) | 30:70 |
| Inlet/outlet temperature | 195° C./95° C. |
| Yield | 66.1% |
| Comment | Spray dried well |
| Product Characterisation | |
| Nature of dry particle | Good |
| Oil encapsulation | Good |
| Oil release | No visible oil at surface |
| Mean droplet size before spraying | 0.95 μm, peaks at 1 μm and 6.5 μm |

EXAMPLE 9

The dispersion was prepared by stirring the biliquid foam and water into the aqueous polymer immediately before spray drying.

| Ingredients | Weight (g) | % |
|---|---|---|
| Preparation 6 | 100 | 11.7 |
| Water | 74.64 | 8.7 |
| Maltodextrin (40% by weight in demineralized water) | 52.5 | 6.1 |
| PVP k30 (30% by weight in demineralized water) | 630 | 73.5 |
| Total | 857.14 | 100 |

| Spray drying conditions | |
|---|---|
| Pilot plant | Tests were carried out in a 1 m diameter pilot spray drying tower with downward co current air flow. Atomisation was carried out with a two fluid nozzle. |
| Total non volatiles | 35% |
| Oil:polymer (dry basis) | 30:70 |
| Inlet/outlet temperature | 175° C./95° C. |
| Yield | 92% |
| Comment | Spray dried well |
| Product Characterisation | |
| Nature of dry particle | Good |
| Oil encapsulation | Good |
| Oil release | Minimal free oil visible on surface. |
| Mean droplet size before spraying | 0.7 μm, peak at 10 μm |

EXAMPLE 10

The dispersion was prepared by stirring the biliquid foam and water into the aqueous polymers immediately before spray drying.

| Ingredients | Weight (g) | % |
|---|---|---|
| Preparation 7 | 89.9 | 11.7 |
| Water | 67.1 | 8.7 |
| Maltodextrin (40% by weight in demineralized water) | 47.2 | 6.1 |
| PVP k30 (30% by weight in demineralized water) | 566.6 | 73.5 |
| Total | 770.9 | 100 |

| Spray drying conditions | |
|---|---|
| Pilot plant | Tests were carried out in a 1 m diameter pilot spray drying tower with downward co current air flow. Atomisation was carried out with a two fluid nozzle. |
| Total non volatiles | 35% |
| Oil:polymer (dry basis) | 30:70 |
| Inlet/outlet temperature | 195° C./90° C. |
| Yield | 93.8% |
| Comment | Spray dried well |
| Product Characterisation | |
| Nature of dry particle | Good |
| Oil encapsulation | Good |
| Oil release | Little visible oil on surface. |
| Mean droplet size before spraying | 2.39 μm, peaks at 1.5 μm and 7.5 μm |

EXAMPLE 11

The dispersion was prepared by stirring the biliquid foam and water into the aqueous polymers immediately before spray drying.

| Ingredients | Weight (g) | % |
|---|---|---|
| Preparation 8 | 67.2 | 11.3 |
| Water | 50.2 | 8.5 |
| Maltodextrin (40% by weight in demineralized water) | 53.3 | 9.0 |
| PVP k30 (30% by weight in demineralized water) | 423.3 | 71.3 |
| Total | 594 | 100 |

| Spray drying conditions | |
|---|---|
| Pilot plant | Tests were carried out in a 1 m diameter pilot spray drying tower with downward co current air flow. Atomisacion was carried out with a two fluid nozzle. |
| Total non volatiles | 35% |
| Oil:polymer (dry basis) | 29:71 |
| Inlet/outlet temperature | 195° C./95° C. |
| Yield | 82.3% |
| Comment | Spray dried well |
| Product Characterisation | |
| Nature of dry particle | Good |
| Oil encapsulation | Good |
| Oil release | No visible free oil |
| Mean droplet size before spraying | 7.26 μm, peak at 11 μm |

EXAMPLE 12

The dispersion was prepared by stirring the biliquid foam and water into the aqueous polymers immediately before spray drying.

| Ingredients | Weight (g) | % |
|---|---|---|
| Preparation 9 | 79.1 | 11.7 |
| Water | 59.1 | 8.7 |
| Maltodextrin (40% by weight in demineralized water) | 41.5 | 6.1 |
| PVP k30 (30% by weight in demineralized water) | 498.5 | 73.5 |
| Total | 678.1 | 100 |

| Spray drying conditions | |
|---|---|
| Pilot plant | Tests were carried out in a 1 m diameter pilot spray drying tower with downward co current air flow. Atomisation was carried out with a two fluid nozzle. |
| Total non volatiles | 35% |
| Oil:polymer (dry basis) | 30:70 |
| Inlet/outlet temperature | 195° C./98° C. |
| Yield | 76.5% |
| Comment | Spray dried well |
| Product Characterisation | |
| Nature of dry particle | Good |
| Oil encapsulation | Good |
| Oil release | Minimal free oil visible on surface. |
| Mean droplet size before spraying | 18.71 μm |

Compression of the powder was performed using a tabletting machine. Successful tablets were produced. The powder was found to withstand high compression forces without affecting the redispersion of the oil droplets upon dissolution in deionised water and the droplet size distribution appeared unaffected.

EXAMPLE 13

The dispersion was prepared by stirring the biliquid foam and water into the aqueous polymers immediately before spray drying.

| Ingredients | Weight (g) | % |
|---|---|---|
| Preparation 10 | 136.11 | 13.61 |
| PVP k30 (40% by weight in demineralized water) | 511.87 | 51.19 |

-continued

| Ingredients | Weight (g) | % |
|---|---|---|
| Water | 295.15 | 29.52 |
| Maltodextrin (40% by weight in demineralized water) | 56.87 | 5.69 |
| Total | 1000 | 100 |

| Spray Drying conditions | |
|---|---|
| Pilot Plane | Tests were carried out in a 1 m diameter pilot spray drying tower with downward co current air flow. Atomisation was carried out with a two fluid nozzle. |
| Total non volatiles | 35% |
| Oil:polymer (dry basis) | 35:65 |
| Inlet/outlet temperature | 210° C./96° C. |
| Yield | 80.40% |
| Comment | Spray dried well |
| Product Characterisation | |
| Nature of dry particle | Good |
| Oil encapsulation | Good |
| Oil release | Good some coalescence |
| Mean droplet size before spraying | 4.0 μm, peak at 8 μm |

EXAMPLE 14

The dispersion was prepared by stirring the biliquid foam and water into the aqueous polymers immediately before spray drying.

| Ingredients | Weight (g) | % |
|---|---|---|
| Preparation 10 | 155.56 | 15.55 |
| PVP k30 (40% by weight in demineralized water) | 472.60 | 47.2 |
| Water | 319.44 | 31.9 |
| Maltodextrin (40% by weight in demineralized water) | 52.5 | 5.25 |
| Total | 1000.1 | 100 |

| Spray Drying conditions | |
|---|---|
| Pilot Plane | Tests were carried out in a 1 m diameter pilot spray drying tower with downward co current air flow. Atomisation was carried out with a two fluid nozzle. |
| Total non volatiles | 35% |
| Oil:polymer (dry basis) | 40:60 |
| Inlet/outlet temperature | 210° C./95° C. |
| Yield | 74.71% |
| Comment | Spray dried well |

| Product Characterisation | |
|---|---|
| Nature of dry particle | Good |
| Oil encapsulation | Good |
| Oil release | Good little coalescence |
| Mean droplet size before spraying | 3.0 μm, peak at 8 μm |

EXAMPLE 15

The dispersion was prepared by stirring the biliquid foam and water into the aqueous polymers immediately before spray drying.

| Ingredients | Weight (g) | % |
|---|---|---|
| Preparation 10 | 175.00 | 17.5 |
| PVP k30 (40% by weight in water) demineralized | 433.12 | 43.31 |
| Water | 343.75 | 38.38 |
| Maltodextrin (40% by weight in demineralized water) | 48.12 | 4.81 |
| Total | 1000 | 100 |

| Spray Drying conditions | |
|---|---|
| Pilot Plant | Tests were carried out in a 1 m diameter pilot spray drying tower with downward co current air flow. Atomisation was carried out with a two fluid nozzle. |
| Total non volatiles | 35% |
| Oil:polymer (dry basis) | 45:55 |
| Inlet/outlet temperature | 210° C./95° C. |
| Yield | 68.69% |
| Comment | Spray dried well, good powder produced. |
| Product Characterisation | |
| Nature of dry particle | Good |
| Oil encapsulation | Appears good from appearance but probably encapsulation lower than expected. |
| Oil release | Good some coalescence |
| Mean droplet size before spraying | 4.0 μm, peak at 8 μm |

EXAMPLE 16

The dispersion was prepared by stirring the biliquid foam and water into the aqueous polymers immediately before spray drying.

| Ingredients | Weight (g) | % |
| --- | --- | --- |
| Preparation 10 | 136.11 | 13.61 |
| Gum acacia (40% by weight in demineralized water) | 568.74 | 56.87 |
| Water | 295.15 | 29.52 |
| Total | 1000 | 100 |

| Spray Drying conditions | |
| --- | --- |
| Pilot Plant | Tests were carried out in a 1 m diameter pilot spray drying tower with downward co current air flow. Atomisation was carried out with a two fluid nozzle. |
| Total non volatiles | 35% |
| Oil:polymer (dry basis) | 35:65 |
| Inlet/outlet temperature | 210° C./95° C. |
| Yield | 82.31% |
| Comment | Spray dried well |
| Product Characterisation | |
| Nature of dry particle | Good |
| Oil encapsulation | Good |
| Oil release | Good but moderate amount of coalescence |
| Mean droplet size before spraying | 4.2 µm, peak at 7.5 µm |

EXAMPLE 17

The dispersion was prepared by stirring the biliquid foam and water into the aqueous polymers immediately before spray drying.

| Ingredients | Weight (g) | % |
| --- | --- | --- |
| Preparation 10 | 136.11 | 13.61 |
| Water | 295.15 | 29.52 |
| Maltodextrin (40% by weight in demineralized water) | 568.74 | 56.87 |
| Total | 1000 | 100 |

| Spray Drying conditions | |
| --- | --- |
| Pilot Plant | Tests were carried out in a 1 m diameter pilot spray drying tower with downward co current air flow. Atomisation was carried out with a two fluid nozzle. |
| Total non volatiles | 35% |
| Oil:polymer (dry basis) | 35:65 |
| Inlet/outlet temperature | 210° C./96° C. |
| Yield | 69.25% |
| Comment | Spray dried well but lower yield than Example 16 |
| Product Characterisation | |
| Nature of dry particle | Moderate |
| Oil encapsulation | Some free oil visible |
| Oil release | Large amount of coalescence |
| Mean droplet size before spraying | 7.4 µm, peak at 9 µm |

EXAMPLE 18

The dispersion was prepared by stirring the biliquid foam and water into the aqueous polymers immediately before spray drying. The dispersion was sheared for 2 minutes on a Silverson disperser before spraying to ensure good mixing.

| Ingredients | Weight (g) | % |
| --- | --- | --- |
| Preparation 11 | 116.67 | 11.66 |
| Modified starch (40% by weight in demineralized water) | 612.5 | 61.25 |
| Water | 270.88 | 27.09 |
| Total | 1000 | 100 |

| Spray Drying conditions | |
| --- | --- |
| Pilot Plant | Tests were carried out in a 1 m diameter pilot spray drying tower with downward co current air flow. Atomisation was carried out with a two fluid nozzle. |
| Total non volatiles | 35% |
| Oil:polymer (dry basis) | 30:70 |
| Inlet/outlet temperature | 210° C./96° C. |
| Yield | 98.70% |
| Comment | Spray dried well |
| Product Characterisation | |
| Nature of dry particle | Good |
| Oil encapsulation | Good |
| Oil release | Good some coalescence |
| Mean droplet size before spraying | 7.6 µm, peak at 8 µm |

"Modified starch" is a chemically modified food starch with a dextrose equivalent value of 32-37%.

EXAMPLE 19

The dispersion was prepared by stirring the biliquid foam and water into the aqueous polymers immediately before spray drying. The dispersion was sheared for 2 minutes on a Silverson disperser before spraying to ensure good mixing.

| Ingredients | Weight (g) | % |
|---|---|---|
| Preparation 12 | 116.67 | 11.66 |
| Modified starch (40% by weight in demineralized water) | 612.5 | 61.25 |
| Water | 270.88 | 27.09 |
| Total | 1000.5 | 100 |

| Spray Drying conditions | |
|---|---|
| Pilot Plant | Tests were carried out in a 1 m diameter pilot spray drying tower with downward co current air flow. Atomisation was carried out with a two fluid nozzle. |
| Total non volatiles | 35% |
| Oil:polymer (dry basis) | 30:70 |
| Inlet/outlet temperature | 210° C./95° C. |
| Yield | 94.06% |
| Comment | Spray dried well |
| Product Characterisation | |
| Nature of dry particle | Good |
| Oil encapsulation | Good |
| Oil release | Good, little coalescence |
| Mean droplet size before spraying | 9.26 µm, peak at 9 µm |

"Modified starch" is a chemically modified food starch with a dextrose equivalent value of 32-37%.

FOOTNOTE TO THE EXAMPLES

| Trade Name | Supplier | INCI Name |
|---|---|---|
| Dow Corning 200 50cst | Dow Corning | Silicone |
| Etocas 25 | Croda Chemicals | PEG-25 Castor Oil |
| Gransil DMCM-5 | Grant Chemicals | Cyclopentasiloxane (D5)(and)Polysilicone-11 (and) Dimethicone. (An Organopolysiloxane mixture) |
| Gransil GCM-5 | Grant Chemicals | Cyclopentasiloxane (D5)(and)Polysilicone-11 (An Organopolysiloxane mixture) |
| Isopar K | Exxon Chemical Ltd | Isoparaffin |
| Kathon ICG 11 | Chesham Chemicals Limited | Mixture of: 5-chloro 2-methyl-4-isothiazolin-3-one and 2-methyl-4-isothiazolin-3-one |
| KMC | Rutgers Kureha Solvents GmbH | Diisopropylnaphthalene isomers (mixture) |
| Mowiol 4-88 | Kuraray Specialties Europe | Polyvinyl alcohol, partly saponified |
| Pergascript red I-6B | Ciba Specialties | Bisindolylphthalide compound |
| Tween 20 | Fisher Chemicals | Polysorbate 20 |

We claim:

1. A discrete powder comprising:
   particles of a matrix of a polymeric material encapsulating droplets of biliquid foam,
   said biliquid foam comprising a continuous phase and an oil phase,
   said droplets having a mean size of 1 to 45 µm, and
   said powder particles having a mean size of 5 to 150 µm.

2. The powder as claimed in claim 1, which is a spray dried powder, a freeze dried powder or a powder produced by fluidized bed granulation.

3. The powder as claimed in claim 1, wherein the polymeric material encapsulating the biliquid foam is selected from the group consisting of carboxymethylcellulose, hydroxyethylcellulose, cetylhydroxycellulose, hydroxypropylcellulose, hydroxylprepylmethylcellulose, hydroxyethylmethylcellulose, methylcellulose, gelatine, gum arabic, gum acacia, gellan gum, shellac, carragenan, natural starch, modified starch, xanthan gum, an alginate, a dextrin, polyvinyl alcohol, polyvinyl acetate, polyvinylpyrollidone, a polyamide and mixtures thereof.

4. The powder as claimed in claim 1, wherein the biliquid foam comprises a substantially water immiscible internal oil phase which comprises a cyclomethicone, dimethicone, phenyl trimethicone, dimethiconol, dimethicone copolyol, trimethylsiloxysilicate, isopropyl isostearate, isopropyl lanolate, isopropyl myristate or isopropyl palmitate, or octyl palmitate, avocado oil, coconut oil, soybean oil or sunflower oil, a caprylic/capric triglyceride, a lanolin oil, orange oil, mineral oil or natural oil, or oleyl alcohol or mixtures thereof.

5. The powder as claimed in claim 4, which comprises from 5% to 50% by weight of an oil, based upon the weight of the powder.

6. A process for the preparation of a discrete powder which comprises a biliquid foam droplets entrapped within a matrix of a polymeric material, which process comprises the steps of:
   i) preparing a biliquid foam wherein the biliquid foam comprises a continuous phase and an oil phase,
   ii) forming a dispersion of the biliquid foam in an aqueous solution, suspension or dispersion of a polymeric material, and
   iii) subjecting the dispersion to drying under conditions such that a discrete powder is formed,
   wherein the droplets have a mean size of 1 to 45 µm, and said powder comprises particles having a mean size of 5 to 150 µm.

7. A process as claimed in claim 6, wherein the drying is carried out by spray drying or freeze drying of the dispersion, or subjecting the dispersion to a fluidized bed granulation process.

8. A process as claimed in claim 6, wherein the biliquid foam has a droplet size of below 12 micrometers.

9. A process as claimed in claim 6, wherein the polymeric material is selected from carboxymethylcellulose, hydroxyethylcellulose, cetylhydroxycellulose, hydroxypropylcellulose, hydroxypropylmethylcellulose, hydroxyethylmethyl cellulose, methylcellulose, gelatine, gum arabic, gum acacia, gellan gum, shellac, carragenan, natural starch, modified starch, xanthan gum, an alginate, a dextrin, polyvinyl alcohol, polyvinyl acetate, polyvinylpyrollidone or a polyamide, or mixtures thereof.

10. A process as claimed in claim 6, wherein the biliquid foam comprises an essentially water immiscible internal oil phase which comprises a cyclomethicone, dimethicone, phenyl trimethicone, dimethiconol, dimethicone copolyol, trimethylsiloxysilicate, isopropyl isostearate, lanolate, myristate or palmitate, octyl palmitate, avocado oil, coconut oil, soybean oil or sunflower oil, a caprylic/capric triglyceride, a lanolin oil, orange oil, mineral oil or natural oil, or oleyl alcohol, or mixtures thereof.

11. A process as claimed in claim 6, wherein the continuous phase of the biliquid foam is an aqueous phase.

12. A process as claimed in claim 6, wherein the aqueous phase includes therein a $C_1$-$C_4$ alcohol or ethylene glycol.

13. A process as claimed in claim 6, wherein the spray drying conditions comprise an inlet temperature in the range of from 170 to 210° C. and an outlet temperature in the range of from 85 to 110° C.

14. A process as claimed in claim 6, wherein the discrete powder is subjected to granulation or formed into tablets.

15. The powder as claimed in claim 1, wherein the biliquid foam comprises a substantially water immiscible internal oil phase which contains one or more fragrances, flavors, deodorizers, perfumes, pharmaceuticals, sunscreens, dyes, pesticides, insect repellents and herbicides.

16. The powder as claimed in claim 15, wherein the substantially water immiscible internal oil phase contains a pharmaceutical.

* * * * *